United States Patent
La Loggia et al.

(10) Patent No.: US 6,794,503 B2
(45) Date of Patent: Sep. 21, 2004

(54) PROCESS FOR THE PREPARATION OF FLUOROSTEROIDS

(75) Inventors: Filippo La Loggia, Gropello Cairoli (IT); Marco Da Col, Bologna (IT)

(73) Assignee: Farmabios S.r.l., Gropello Cairoli (IT)

( * ) Notice: Subject to any disclaimer, the term of this patent is extended or adjusted under 35 U.S.C. 154(b) by 0 days.

(21) Appl. No.: 09/858,692

(22) Filed: May 16, 2001

(65) Prior Publication Data

US 2002/0062021 A1 May 23, 2002

(30) Foreign Application Priority Data

Nov. 17, 2000 (IT) .................................... MI2000A2475

(51) Int. Cl.$^7$ .............................................. C07J 71/00
(52) U.S. Cl. ........................................ 540/87; 540/88
(58) Field of Search ....................... 540/87, 88; 552/610

(56) References Cited

U.S. PATENT DOCUMENTS

| | | | | |
|---|---|---|---|---|
| 2,838,548 A | * | 6/1958 | Schneider et al. .......... | 552/565 |
| 2,961,441 A | | 11/1960 | Bogert et al. | |
| 3,207,751 A | * | 9/1965 | Pinson, Jr. .................. | 540/23 |
| 3,557,158 A | * | 1/1971 | Lincoln et al. ......... | 260/397.45 |
| 3,980,778 A | | 9/1976 | Ayer et al. | |
| 4,188,322 A | * | 2/1980 | Castell et al. .......... | 260/239.55 |
| 4,255,331 A | * | 3/1981 | MacDonald ............. | 260/239.5 |
| 4,619,921 A | * | 10/1986 | Kalvoda et al. ............ | 514/180 |
| 5,478,957 A | * | 12/1995 | Godard et al. ............. | 552/610 |
| 5,556,965 A | * | 9/1996 | Godard et al. ................ | 540/87 |

* cited by examiner

Primary Examiner—Sabiha Qazi
(74) Attorney, Agent, or Firm—Hedman & Costigan, P.C.

(57) ABSTRACT

Described herein is a process for the preparation of 6α-fluorosteroids of formula (I), in which R is chosen from H, OH and an alkyl group with from 1 to 4 carbon atoms and R' is a carboxyalkyl group with from 1 to 4 carbon atoms in the alkyl chain, comprising the selective fluorination at the 6α-position

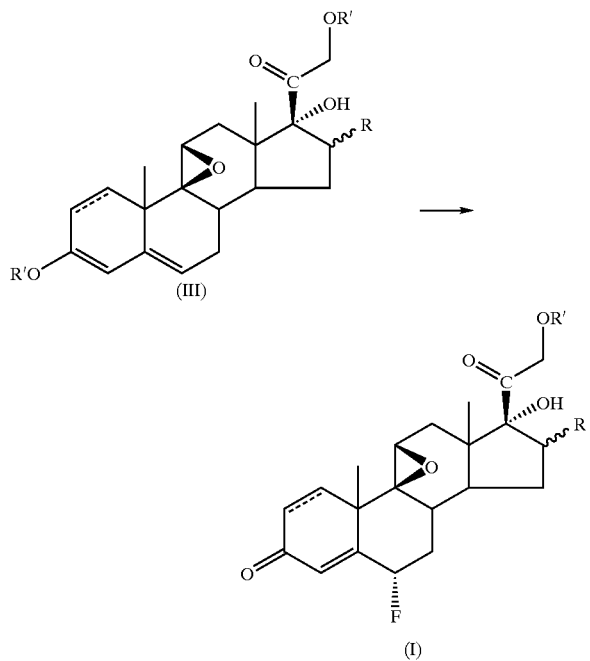

by treatment of the compound of formula (III), wherein R and R' are as defined above, with an electrophilic fluorinating agent.

5 Claims, No Drawings

PROCESS FOR THE PREPARATION OF FLUOROSTEROIDS

FIELD OF THE INVENTION

The present invention refers to a stereoselective process for the preparation of 6α-fluorosteroids of formula (I) reported hereinafter, useful in the preparation of anti-inflammatory pharmaceutical formulations.

PRIOR ART

The availability of a process for the preparation of pregnane fluoro derivatives, which might predominantly yield 6β-fluoro substituted isomers, well known anti-inflammatory agents, is very important from a pharmacological point of view, since the corresponding 6β-fluoro derivatives do not exert any pharmacological action.

Many procedures for the preparation of 6-fluoro pregnane derivatives have been developed so far; however, all of them yield mixtures of the two isomers in relatively high 6β/6α ratios. It follows that the conversion of isomer 6β into isomer 6α or repeated purifications are required to obtain the pharmacologically active isomer only.

By way of example, U.S. Pat. No. 2,961,441 discloses the preparation of 6β-fluoro-3-keto-Δ⁴-pregnenes by fluorination of the corresponding 3-enol esters with perchloryl fluoride, in an inert organic solvent and in the presence of a catalyst. In particular, said patent describes the fluorination on 3,17α,21-triacetoxy derivative. The process yields 6β-fluoro substituted compounds, which are converted into the corresponding 6α isomers by methods known in the art.

U.S. Pat. No. 3,980,778 describes the preparation of the 6α,9α-difluoro pregnane derivative of formula

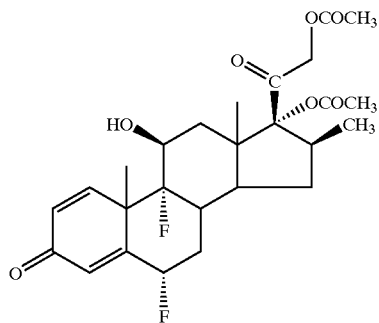

by fluorination, with perchloryl fluoride, of 3,17α,21-trihydroxy-16β-methylpregna-3,5,9-(11)-trien-20-one 3,17,21-triacetate, obtained by causing to react the corresponding 17α,21-dihydroxy-16β-methylpregna-4,9(11)-diene-3,20-dione 21 acetate with isopropenyl acetate.

Said process yields a 6β/6α isomeric mixture in which isomer 6β predominates. It follows that, with a view to obtaining a pharmaceutically useful final product, the 6β-fluorosteroid is to be converted into the corresponding 6α-fluoro compound.

In all aforementioned cases, the formation of 3-enol ester, necessary for the steroid activation at the 6-position, brings about the simultaneous acetylation of the hydroxy groups, if any, at 17α- and 21-positions.

Said processes suffer from a number of disadvantages; for example they are not stereoselective and require the use of perchloryl fluoride as a fluorinating agent, an esplosive and highly corrosive reagent that must be handled with special care and must be used with very long reaction times.

The use of other fluorinating agents, such as for example Selectfluor®, Accufluor® NFSi or Accufluor® NFTh, on the described substrates yields mixtures with still more unfavourable 6α:6β ratios.

Therefore, the need for a process for the preparation of 6α-fluorosteroids, free from the disadvantages of the processes known in the art, is deeply felt.

SUMMARY

It has surprisingly been found that a high stereoselectivity of the fluorination at the 6-position can be obtained by operating on substrates obtained in order that the 17α-hydroxy group remains unreacted, and by using specific fluorinating agents. It is, therefore, an object of the present invention to provide a process for the preparation of 6α-fluorosteroids of formula (I)

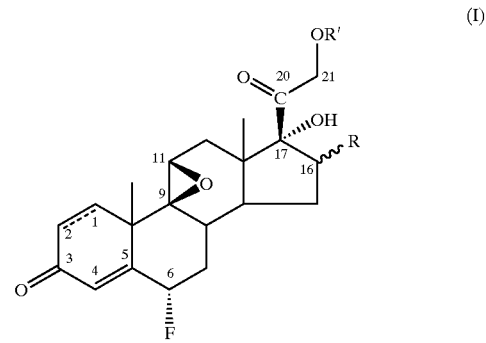

wherein R is a substituent at the α- or β-position, chosen from H, OH and an alkyl group with from 1 to 4 carbon atoms, R' is a carboxyalkyl group with from 1 to 4 carbon atoms in the alkyl chain and wherein a double bond may be present between positions 1 and 2, said process comprising the reaction of the compound of formula (III) with an electrophilic fluorinating agent to give the compound of formula (I)

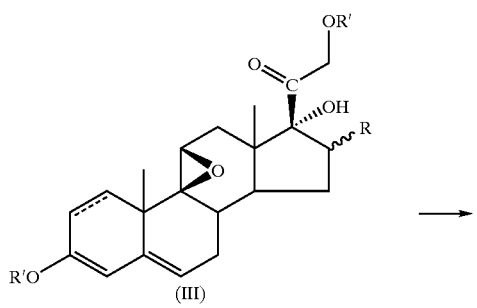

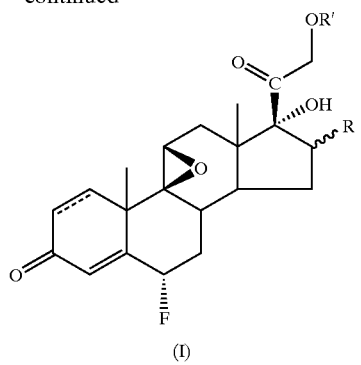

(I)

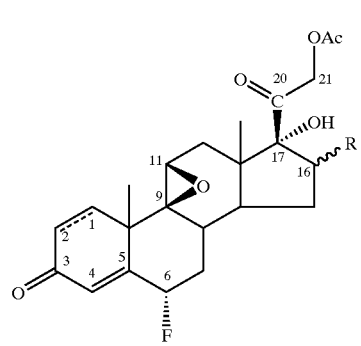

(I)

wherein R and R' are as defined above, and wherein said electrophilic fluorinating agent is selected from the group consisting of N-fluoro N-chloromethyl triethylenediamine bis-tetrafluoroborate, 1-fluoro-4-hydroxy-1,4-diazabicyclo[2.2.2]octane-bis-tetrafluoroborate, and 1-fluoro-benzenesulfonamide.

The characteristics and advantages of the process of the present invention will be apparent from the detailed description reported herein.

DETAILED DESCRIPTION OF THE INVENTION

The fluorination reaction of the present invention is carried out on the compound of formula (III) using—as a fluorinating agent—an electrophilic fluorinating agent, selected from the group consisting of Selectfluor® (i.e. N-fluoro N-chloromethyl triethylenediamine bis-tetrafluoroborate), Accufluor® NFTh (i.e. 1-fluoro-4-hydroxy-1,4-diazabicyclo[2.2.2]octane-bis-tetrafluoroborate), and Accufluor® NFSi (i.e. 1-fluoro-benzenesulfonamide), and preferably Selectfluor®.

The reaction solvent used may be any solvent in which the fluorinating agent is soluble; for example, the reaction can be carried out in the presence of Accufluor® NFTh or Selectfluor® using dimethylformamide or acetonitrile as a solvent.

The fluorination reaction of the present invention is typically carried out at a temperature ranging from −20° C. to +50° C., and preferably from 0° C. to 30° C.

At the aforementioned fluorination conditions, the deprotection of the 3-ketonic function takes place simultaneously.

The fluorine position in the compound of formula (I) obtained by fluorination definitely favours isomer 6α a since the 6α:6β ratio is higher than 90:10.

The process of the invention may be used for example to prepare the compound of formula (I) wherein R' is an acetyl group:

wherein R is defined as above.

The compound of formula (III), which is used as a substrate for the fluorination of the invention to obtain the compound of formula (I) wherein R' is an acetyl group, can be obtained, e.g. by a single treatment of the compound of formula (II) with isopropenyl acetate, wherein the protection of the hydroxylic function at the 21-position and of the ketonic function at the 3-position takes place:

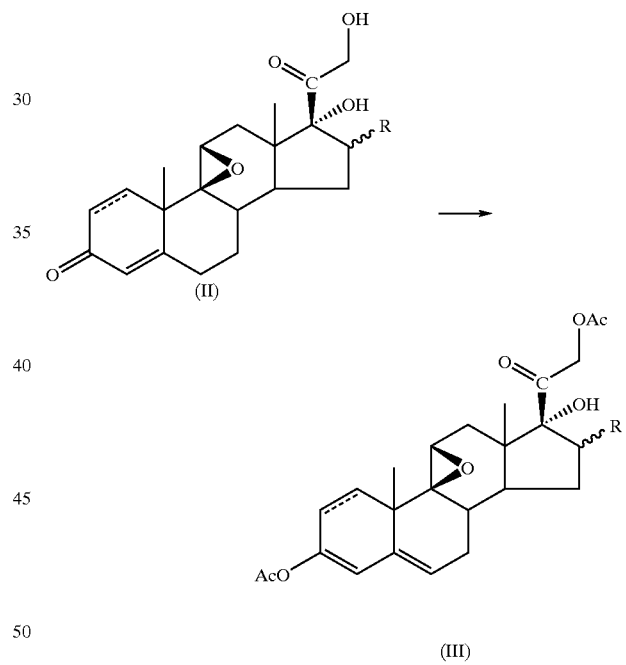

wherein R is as defined above and Ac is an acetyl group.

In said acetylation reaction, isopropenyl acetate may have the double function of reagent and sole reaction solvent; otherwise, the reaction may be carried out using isopropenyl acetate as reagent, with addition of a solvent.

Other compounds of formula (III) in which R' is different from an acetyl group, used as substrates for the fluorination of the invention, can be obtained according to processes known in the art.

Starting from the compound of formula (I), obtained as described above, it is possible to obtain the corresponding compounds of formula (I') by processes known in the art:

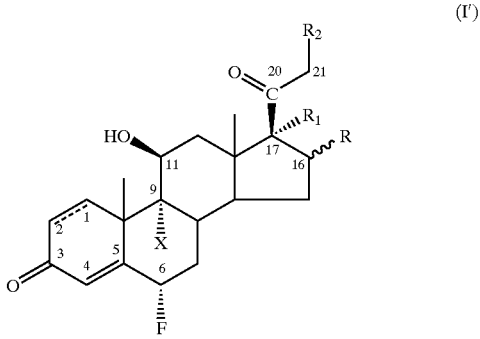

(I')

wherein R is a substituent at the α- or β-position, chosen from H, OH and an alkyl group with from 1 to 4 carbon atoms; $R_1$ is chosen from H, OH and a carboxyalkyl group containing 1 to 4 carbon atoms in the alkyl chain; or R and $R_1$, taken together, form a double bond or a

group, where A and B, equal or different from each other, are H or an alkyl group with from 1 to 4 carbon atoms; $R_2$ is chosen from H, OH and a carboxyalkyl group with from 1 to 4 carbon atoms; X is chosen from H, F, Cl and Br; and where a double bond may be present between positions 1 e 2.

The following examples are conveyed by way of indication, not of limitation, of the present invention.

EXAMPLE 1

Preparation of 6α-fluoro-9β,11β-epoxy-17α-hydroxy-16β-methylpregna-1,4-diene-3,20-dione 21-acetate 9β,11β-epoxy-17α,21-dihydroxy-16β-methylpregna-1,4-diene-3,20-dione (15 g) was added under stirring and nitrogen atmosphere to a solution previously heated to 55° C., and prepared with isopropenyl acetate (135 ml) and p-toluenesulfonic acid (0.6 g). The reaction was continued for 60 min at 80° C., then the temperature was decreased to 50° C. The resulting mixture was buffered with triethylamine (0.48 ml), added with acetonitrile (15 ml), concentrated under vacuum to small volume, and added with further acetonitrile (150 ml).

The resulting solution was cooled to 0° C. in a $N_2$ atmosphere and added portionwise with Accufluor® NFTh (13 g). The reaction was continued for 12 hrs at 0° C. in a $N_2$ atmosphere to give a suspension, wherefrom a solid product separated by filtration. The solid obtained was added with demineralised water (150 ml) and with a 32% ammonia aqueous solution to a pH value of 7–7.5. Filtration followed by drying under vacuum at 60° C. gave 11 g of the captioned product.

HPLC analysis on the solid product revealed a 6α:6β ratio of 93.5:6.5.

EXAMPLE 2

Preparation of 17α-hydroxy-9β,11β-epoxy-16α-methylpregna-1,3,5-triene-20-one-3,21-diacetate 9β,11β-epoxy-17α,21 -dihydroxy-16α-methylpregna-1,4-diene-3,20-dione (10 g) was added under stirring and nitrogen atmosphere to a solution previously heated to 55° C., and prepared with isopropenyl acetate (90 ml) and p-toluenesulfonic acid (0.4 g). The reaction was continued for 60 min at 80° C., then the temperature was decreased to 50° C. The resulting mixture was buffered with triethylamine (0.32 ml), added with acetonitrile (10 ml), concentrated under vacuum to small volume, and diluted with absolute ethanol (60 ml).

The resulting solution was precipitated in demineralised water (600 ml) to give a solid precipitate that was separated from the liquid by filtration. Oven-drying under vacuum at 40° C. gave 12.2 g of the captioned product.

The solid product purity determined by HPLC at 310 nm was 89.9%. The captioned product was characterised by $^1$H-NMR (CDCl$_3$ 200 MHz) δ 0.91 (d, 3H, J=7 Hz), 0.93 (s, 3H), 1.25 (s, 3H), 2.18 (s, 3H), 2.19 (s, 3H), 3.04 (s, 1H), 4.87 (system AB, J=18 Hz, 2H), 5.46 (d, J=10 Hz, 1H), 5.69 (dd, J=1.8, 10 Hz, 1H), 5.77 (t, 1H), 5.80 (s, 1H).

EXAMPLE 3

Preparation of 6α-fluoro-9β,11β-epoxy-17α-hydroxy-16α-methylpregna-1,4-diene-3,20-dione 21-acetate 17α-hydroxy-9β,11β-epoxy-16α-methylpregna-1,3,5-triene-20-one3,21-diacetate (5 g), prepared as per Example 2, was added in a $N_2$ atmosphere and under stirring to acetonitrile (50 ml) previously cooled to 0° C. The resulting solution was added portionwise with Selectfluor® (F-TEDA.BF$_4$) (3.7 g). The reaction was continued for 12 hrs at 0° C. in a $N_2$ atmosphere to give a suspension, wherefrom a solid product separated by filtration. The solid obtained was added with demineralised water (50 ml) and with a 32% ammonia aqueous solution to a pH value of 7–7.5. Filtration followed by drying under vacuum at 60° C. gave 2.6 g of the captioned product. HPLC analysis on the solid product revealed a 6α:6β ratio of 94.5:5.5.

EXAMPLE 4

Preparation of 6α-fluoro-9β,11β-epoxy-17α-hydroxy-16β-methylpregna-1,4-diene-3,20-dione 21-acetate 9β,11β-epoxy-17α,21-dihydroxy-16β-methylpregna-1,4-diene-3,20-dione (15 g) was added under stirring in a $N_2$ atmosphere to a solution previously heated to 55° C., and prepared with isopropenyl acetate (135 ml) and p-toluenesulfonic acid (0.6 g). The reaction was continued for 60 min at 80° C., then the temperature was decreased to 50° C. The resulting mixture was buffered with triethylamine (0.48 ml), added with acetonitrile (15 ml), concentrated under vacuum to small volume, and added with further acetonitrile (150 ml).

The resulting solution was cooled to 0° C. in a $N_2$ atmosphere and added portionwise with Selectfluor® (13 g). The reaction was continued for 12 hrs at 0° C. in a $N_2$ atmosphere to give a suspension, wherefrom a solid product separated by filtration. The solid obtained was added with demineralised water (150 ml) and with a 32% ammonia aqueous solution to a pH value of 7–7.5. Filtration followed by drying under vacuum at 60° C. gave 10.5 g of the captioned product. HPLC analysis on the solid product revealed a 6α:6β ratio of 93:7.

EXAMPLE 5

Preparation of 6α-fluoro-9β,11β-epoxy-17α-hydroxy-16α-methylpregna-1,4-diene-3,20-dione 21-acetate 9β,11β-epoxy-17α,21-dihydroxy-16α-methylpregna-1,4-diene-3,20-dione (15 g) was added under stirring in a $N_2$ atmosphere to a solution previously heated to 55° C., and prepared with isopropenyl acetate (135 ml) and p-toluenesulfonic acid (0.6 g). The reaction was continued for 60 min at 80° C., then the temperature was decreased to 50° C. The resulting mixture was buffered with triethylamine (0.48 ml), added with acetonitrile (15 ml), concentrated under vacuum to small volume, and added with further acetonitrile (150 ml).

The resulting solution was cooled to 0° C. in a $N_2$ atmosphere, added with demineralised water (3 ml) and, portionwise, with Selectfluor® (13 g). The reaction was continued for 12 hrs at 0° C. in an $N_2$ atmosphere to give a suspension, wherefrom a solid product separated by filtration. The solid obtained was added with demineralised water (150 ml) and with a 32% ammonia aqueous solution to a pH value of 7–7.5. Filtration followed by drying under vacuum at 60° C. gave 11.4 g of the captioned product.

HPLC analysis on the solid product revealed a 6α:6β ratio of 94.4:5.6.

EXAMPLE 6

Preparation of 6α-fluoro-9β,11β-epoxy-17α-hydroxy-16α-methylpregna-1,4-diene-3,20-dione 21-acetate 9β,11β-epoxy-17α,21-dihydroxy-16α-methylpregna-1,4-diene-3,20-dione (15 g) was added under stirring in a $N_2$ atmosphere to a solution previously heated to 55° C., and prepared with isopropenyl acetate (135 ml) and methanesulfonic acid (0.22 g). The reaction was continued for 60 min at 80° C., then the temperature was decreased to 50° C. The resulting mixture was buffered with triethylamine (0.48 ml), added with acetonitrile (15 ml), concentrated under vacuum to small volume, and added with further acetonitrile (150 ml).

The resulting solution was cooled to 0° C. in a $N_2$ atmosphere and added portionwise with Selectfluor® (13 g). The reaction was continued for 12 hrs at 0° C. in a $N_2$ atmosphere to give a suspension, wherefrom a solid product separated by filtration. The solid obtained was added with demineralised water (150 ml) and with a 32% ammonia aqueous solution to a pH value of 7–7.5. Filtration followed by drying under vacuum at 60° C. gave 12.4 g of the captioned product.

HPLC analysis on the solid product revealed a 6α:6β ratio of 94.8:5.2.

EXAMPLE 7

Preparation of 6α-fluoro-9β,11β-epoxy-17α-hydroxy-16α-methylpregna-1,4-diene-3,20-dione 21-acetate 9β,11β-epoxy-17α,21-dihydroxy-16α-methylpregna-1,4-diene-3,20-dione (50 g) was added under stirring in a $N_2$ atmosphere to a solution previously heated to 55° C., and prepared with isopropenyl acetate (450 ml) and p-toluenesulfonic acid (2 g). The reaction was continued for 60 min at 80° C., then the temperature was decreased to 50° C. The resulting mixture was buffered with triethylamine (1.6 ml), added with acetonitrile (50 ml), concentrated under vacuum to small volume, and added with further acetonitrile (500 ml).

The resulting solution was cooled to 0° C. in a $N_2$ atmosphere and added portionwise with Selectfluor® (43 g). The reaction was continued for 12 hrs at 0° C. in a $N_2$ atmosphere to give a suspension, wherefrom a solid product separated by filtration. The solid obtained was added with demineralised water (500 ml) and with a 32% ammonia aqueous solution to a pH value of 7–7.5. Filtration followed by drying under vacuum at 60° C. gave 39.2 g of the captioned product. HPLC analysis on the solid product revealed a 6α:6β ratio of 94.9:5.1.

EXAMPLE 8

Preparation of 6α-fluoro-9β,11β-epoxy-17α-hydroxy-pregna-1,4-diene-3,20-dione 21-diacetate 9β,11β-epoxy-17α,21-dihydroxy-pregna-1,4-diene-3,20-dione (15 g) was added under stirring in a $N_2$ atmosphere to a solution previously heated to 55° C., and prepared with isopropenyl acetate (135 ml) and p-toluenesulfonic acid (0.3 g). The reaction was continued for 60 min at 80° C., then the temperature was decreased to 50° C. The resulting mixture was buffered with triethylamine (0.24 ml), added with acetonitrile (15 ml), concentrated under vacuum to small volume, and added with further acetonitrile (150 ml).

The resulting solution was cooled to approx. 0° C. in a $N_2$ atmosphere and added portionwise with Selectfluor® (13 g). The reaction was continued for 12 hrs at 0° C. in a $N_2$ atmosphere to give a suspension, wherefrom a solid product separated by filtration. The solid obtained was added with demineralised water (150 ml) and with a 32% ammonia aqueous solution to a pH value of 7–7.5. Filtration followed by drying under vacuum at 60° C. gave 9 g of the captioned product.

HPLC analysis on the solid product revealed a 6α:6β ratio of 96:4.

What is claimed is:
1. Process for the preparation of 6α-fluorosteroids of formula (I)

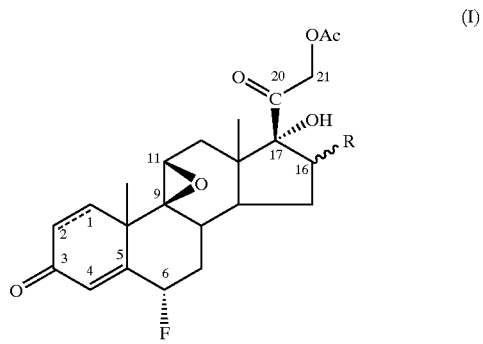

wherein R is a substituent at the α- or β-position, chosen from H, OH and an alkyl group with from 1 to 4 carbon atoms, Ac is an acetyl group, and wherein a double bond may be present between positions 1 and 2, said process comprising:

reaction of the compound of formula (II) with isopropenyl acetate to obtain the compound of formula (III) wherein R is as defined above;

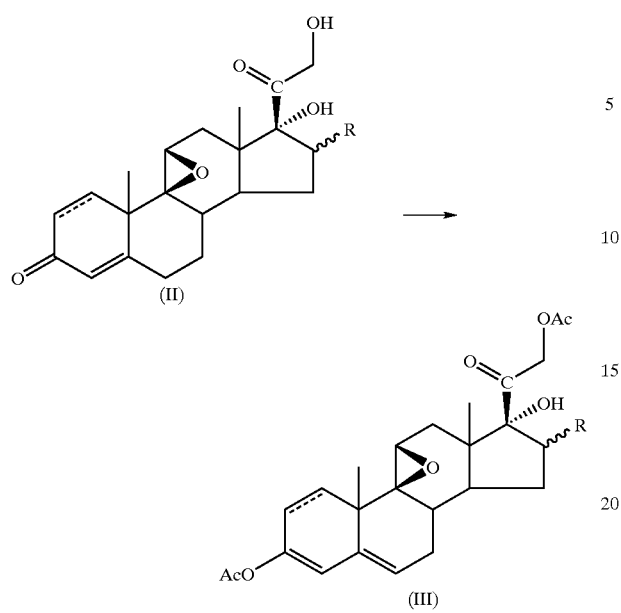

reaction of the compound of formula (III) with an electrophilic fluorinating agent to give the compound of formula (I)

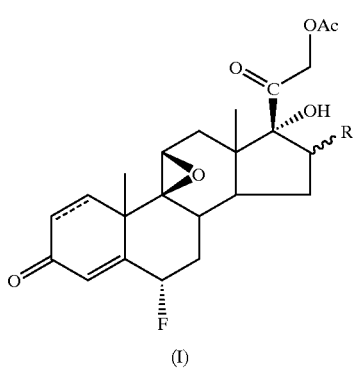

wherein R is as defined above, and wherein said electrophilic fluorinating agent is selected from the group consisting of N-fluoro N-chloromethyl triethylenediamine bis-tetrafluoroborate, 1-fluoro-4-hydroxy-1,4-diazabicyclo[2.2.2]octane-bis-tetrafluoroborate, and 1-fluoro-benzenesulfonamide.

2. The process according to claim 1, wherein said electrophilic fluorinating agent is N-fluoro N-chloromethyl triethylenediamine bis-tetrafluoroborate.

3. The process according to claim 1, wherein said electrophilic fluorinating agent is 1-fluoro-4-hydroxy-1,4-diazabicyclo[2.2.2]octane-bis-tetrafluoroborate.

4. The process according to claim 1, wherein said reaction with the electrophilic fluorinating agent is carried out at a temperature ranging from −20° C. to +50° C.

5. The process according to claim 1, wherein said temperature ranges from 0° C. to +30° C.

* * * * *